US012572212B2

(12) United States Patent
Shin et al.

(10) Patent No.: US 12,572,212 B2
(45) Date of Patent: Mar. 10, 2026

(54) GENERATING DEVICE IDENTIFIERS AND DEVICE CONTROLS BASED ON HAND GESTURES

(71) Applicant: GOOGLE LLC, Mountain View, CA (US)

(72) Inventors: Dongeek Shin, Santa Clara, CA (US); Ricardo John Campbell, Redwood City, CA (US)

(73) Assignee: GOOGLE LLC, Mountain View, CA (US)

( * ) Notice: Subject to any disclaimer, the term of this patent is extended or adjusted under 35 U.S.C. 154(b) by 88 days.

(21) Appl. No.: 17/656,707

(22) Filed: Mar. 28, 2022

(65) Prior Publication Data

US 2023/0305630 A1 Sep. 28, 2023

(51) Int. Cl.
*G06F 3/01* (2006.01)
*A61B 5/024* (2006.01)
(Continued)

(52) U.S. Cl.
CPC .......... *G06F 3/017* (2013.01); *A61B 5/02416* (2013.01); *G06F 1/163* (2013.01);
(Continued)

(58) Field of Classification Search
CPC . G06F 3/01; G06F 3/014; G06F 3/017; G06F 1/163; G06V 40/28; H04L 67/52
See application file for complete search history.

(56) References Cited

U.S. PATENT DOCUMENTS

2003/0187337 A1 * 10/2003 Tarassenko ........... G06F 18/256
600/300
2010/0329509 A1 * 12/2010 Fahn .................... G06V 40/113
382/103
(Continued)

OTHER PUBLICATIONS

Tyler Freeman, "Training For Machine Learning Models to Personalize Gestures in Wearable and Mobile Devices", Apr. 5, 2019, Technical Disclosure Commons, Defensive Publications Series, pp. 1-8 (Year: 2019).*
(Continued)

*Primary Examiner* — Nicholas Klicos
(74) *Attorney, Agent, or Firm* — Brake Hughes Bellermann LLP

(57) ABSTRACT
Techniques of controlling electronic devices using gestures use a wearable device on a user which translates, via a model, user movements into signals that both identify an electronic device to be controlled and a specific action to take with regard to that electronic device. The wearable device includes an inertial measurement unit (IMU) sensor and a photoplethysmography (PPG) sensor and measure six degrees of freedom (6DOF). The model is a convolutional neural network (CNN) that takes x, y, and z-acceleration signals generated by the IMU and PPG and places each acceleration component generated from each sensor in a separate channel. The CNN takes the input from each channel and generates a respective, separate model for each channel. The output at each of the stacked layers are combined in a fully connected layer to produce CNN output identifying an electronic device and a control for the electronic device.

19 Claims, 8 Drawing Sheets

(51) Int. Cl.
   G06F 1/16         (2006.01)
   G06N 3/04         (2023.01)
   G06V 40/20       (2022.01)

(52) U.S. Cl.
   CPC ............... G06F 3/014 (2013.01); G06N 3/04
   (2013.01); G06V 40/28 (2022.01)

(56)             References Cited

U.S. PATENT DOCUMENTS

| | | | | |
|---|---|---|---|---|
| 2015/0077336 | A1* | 3/2015 | Elangovan | G06F 3/014 |
| | | | | 345/156 |
| 2016/0099010 | A1* | 4/2016 | Sainath | G10L 15/16 |
| | | | | 704/232 |
| 2017/0060254 | A1* | 3/2017 | Molchanov | G06N 3/082 |
| 2017/0169315 | A1* | 6/2017 | Vaca Castano | G06V 10/25 |
| 2017/0220854 | A1* | 8/2017 | Yang | G06V 20/46 |
| 2018/0129906 | A1* | 5/2018 | Habibian | G06V 10/764 |
| 2018/0324595 | A1* | 11/2018 | Shima | H04B 7/0413 |
| 2019/0034714 | A1* | 1/2019 | Barth | G06V 40/113 |
| 2019/0286233 | A1* | 9/2019 | Newberry | A61B 5/0075 |
| 2019/0294860 | A1* | 9/2019 | Jin | G06N 3/045 |
| 2020/0019921 | A1* | 1/2020 | Buibas | G06V 20/52 |
| 2020/0026347 | A1* | 1/2020 | El Kaliouby | G06V 40/176 |
| 2020/0242421 | A1* | 7/2020 | Sobhany | G06N 20/00 |
| 2020/0319713 | A1 | 10/2020 | Huffman et al. | |
| 2021/0005071 | A1* | 1/2021 | Sharma | A61B 5/1121 |
| 2021/0142214 | A1* | 5/2021 | Maalouf | G06F 3/017 |
| 2021/0158630 | A1* | 5/2021 | Muhammad | G06F 3/017 |
| 2021/0349542 | A1 | 11/2021 | Cipoletta et al. | |
| 2022/0006892 | A1* | 1/2022 | Perkins | G06F 3/044 |
| 2022/0249906 | A1* | 8/2022 | Phillips | G06N 3/045 |
| 2022/0391760 | A1* | 12/2022 | Fedulova | G06N 20/20 |

OTHER PUBLICATIONS

International Search Report and Written Opinion for PCT Application No. PCT/US2023/064704, mailed on Jun. 15, 2023, 15 pages.

* cited by examiner

200

Computer 120

Network Interface 222

Processing Units 224

Display Interface 228

Memory 226

| Signal Manager 230 | Prediction Engine Manager 240 |
|---|---|

Signal Data 231

IMU Data 232

| Component 232(1) | ... | Component 232(M) |
|---|---|---|

PPG Data 233

| Component 232(1) | ... | Component 233(N) |
|---|---|---|

Context Data 233

Compass Data 234

Camera Data 235

GPS Data 236

Device and Control Manager 250

Device Identification Data 251

Device Control Data 252

Resolution Data 253

Prediction Engine Data 241

Stacked Layer Data 242

Channel Data 242(1)

Channel Data 242(2)

...

Channel Data 242(P)

Model Data 243

Channel Model Data 243(1)

Convolutional Layer 243(1)(1)

...

Convolutional Layer 243(1)(R1)

FC Layer Data 244

Output Layer Data 245

FIG. 2

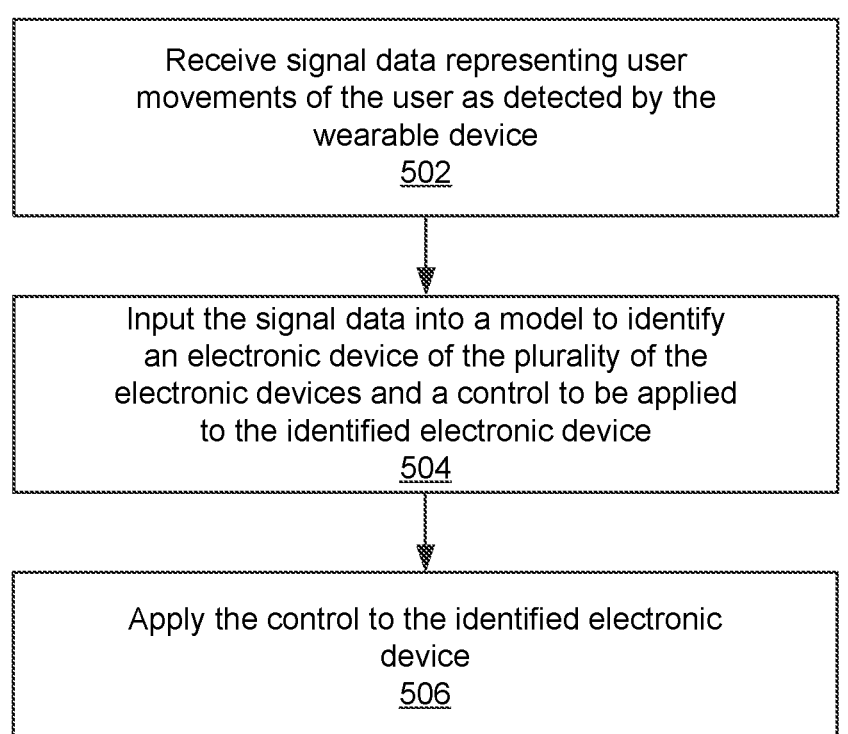
500
Receive signal data representing user
movements of the user as detected by the
wearable device
502
Input the signal data into a model to identify
an electronic device of the plurality of the
electronic devices and a control to be applied
to the identified electronic device
504
Apply the control to the identified electronic
device
506
FIG. 5

GENERATING DEVICE IDENTIFIERS AND DEVICE CONTROLS BASED ON HAND GESTURES

TECHNICAL FIELD

This description relates to gesture-based remote control of electronic devices.

BACKGROUND

Some user environments include multiple electronic devices placed in an arrangement in the vicinity of a user. For example, a home or office environment may have multiple screens, room light controllers, a thermostat, door-bell and/or security cameras, a garage door, and smart appliances such as a refrigerator, oven, microwave, and dishwasher. In such a user environment, the user may wish to control all of the multiple electronic devices in the environment. For example, each of the electronic devices may have a respective remote control by which the user is able to control the electronic devices, e.g., changing the channel on a television, raising the volume of the television, pre-heating an oven, adding 30 seconds cooking time to a microwave oven, setting a thermostat to a higher tempera-ture, turn the lights on or off and/or dim to a desired level, and so on.

SUMMARY

Implementations described herein are related to providing a universal gesture-based remote control of multiple elec-tronic devices. While there are examples of gesture-based remote control of a single electronic device. For multiple devices in a vicinity of a user, however, there may be complications. For example, consider a user in a room with a television, a sound system, a microwave oven, and light-ing, and the user wishes to dim the lighting. A gesture-based remote control that is configured to control all the devices in the room identifies, from a gesture formed by the user, which device the user intends to control and the type of control for the selected device. For this gesture-based remote control, the user is provided a wearable device, e.g., a wristband with inertial measurement unit (IMU) and photoplethysmography (PPG) sensors to generate gesture signals based on specific gestures. Data from these signals is input into a machine learning engine, specifically a convolutional neural network (CNN) to identify the device and control selected by the user. The CNN used for this remote control uses separate channels for each respective signal source (IMU, PPG) and each degree of freedom (x,y,z) such that the CNN uses a respective distinct model for each channel; the outputs of the distinct models are combined at a fully connected layer of the CNN to produce output identifying a device and a control.

In one general aspect, a computer-based method can include receiving, by a computer from a wearable device worn by a user, the computer having a connection to a network to which a plurality of electronic devices are connected, signal data representing user movements of the user as detected by the wearable device. The method can also include inputting the signal data into a model to identify an electronic device of the plurality of the electronic devices and a control to be applied to the identified electronic device, the model including a neural network configured to take as input the signal data and produce as output a device iden-tifier of the identified electronic device and a control identifier identifying the control. The method can further include applying the identified control to the identified electronic device.

In another general aspect, a computer program product comprises a non-transitory storage medium, the computer program product including code that, when executed by processing circuitry of a computing device, causes the processing circuitry to perform a method. The method can include receiving, by a computer from a wearable device worn by a user, the computer having a connection to a network to which a plurality of electronic devices are connected, signal data representing user movements of the user as detected by the wearable device. The method can also include inputting the signal data into a model to identify an electronic device of the plurality of the electronic devices and a control to be applied to the identified electronic device, the model including a neural network configured to take as input the signal data and produce as output identifiers of an electronic device. The method can further include applying the identified control to the identified electronic device.

In another general aspect, an electronic apparatus com-prises memory and controlling circuitry coupled to the memory. The controlling circuitry can be configured to receive, from a wearable device worn by a user, the user located in a vicinity of a plurality of electronic devices, signal data representing user movements of the user as detected by the wearable device. The controlling circuitry can also be configured to input the signal data into a model to identify an electronic device of the plurality of the electronic devices and a control to be applied to the identi-fied electronic device, the model including a neural network configured to take as input the signal data and produce as output identifiers of an electronic device. The controlling circuitry can further be configured to apply the identified control to the identified electronic device.

The details of one or more implementations are set forth in the accompanying drawings and the description below. Other features will be apparent from the description and drawings, and from the claims.

BRIEF DESCRIPTION OF THE DRAWINGS

FIG. 2 is a diagram that illustrates an example electronic environment in which the improved techniques described herein may be implemented.

FIG. 5 is a flow chart that illustrates an example method of controlling multiple electronic devices, according to disclosed implementations.

DETAILED DESCRIPTION

Figure 1A:
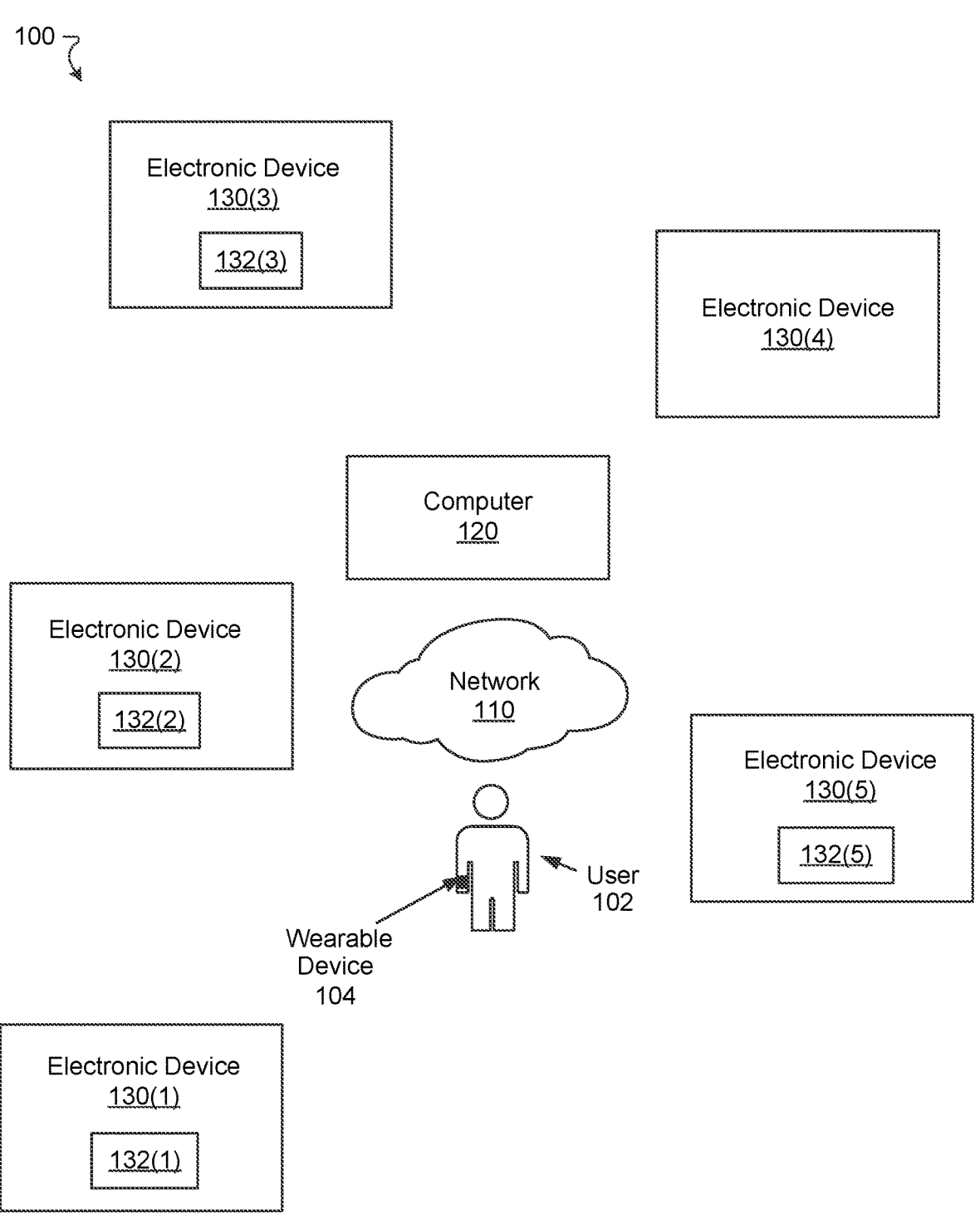
FIG. 1A is a diagram that illustrates an example environ-ment in which improved techniques described herein may be implemented.

Some electronic environments have multiple electronic devices that are not compatible and are at different distances or locations from the user. Because the multiple electronic devices may not be compatible and are at different distances or locations, they may be controlled using different remote control systems. Handling different remote controls to control each of the multiple electronic device can be inconvenient. Moreover, such remote controls for some of the multiple electronic devices may require line-of-sight placement with respect to the user. Because some of the multiple electronic devices may not be physically located in the same room, a user may not be able to control, from a single room location, some of the electronic devices that require line-of-sight control.

The challenges associated with the electronic environments described above may be addressed, to some extent, with more recent developments. For example, some conventional electronic devices may be controlled using voice commands. Conventional remote control systems such as voice-activated systems address issues presented by remote controls associated with each electronic device; for example, a user may activate a lighting control with a first voice command, e.g., "lights," and then the user may issue a second voice command, "off," to shut off the lights.

Nevertheless, there can be issues related to the use of such electronic devices. For example, voice controls may be problematic outside of a private home environment; people may not be comfortable issuing voice commands in a public setting. As another example, gestures and/or voice commands targeted to one device in the environment may inadvertently control a second device.

Some conventional remote control systems make use of hand gestures from a user to identify a control for an electronic device. For example, a device may have a built-in camera that can form an image of a gesture and determine the control from the image. A technical problem with the above-described conventional remote control systems is that a camera requires line-of-sight directions from the user, which may not always be possible. Another technical problem with the above-described conventional remote control systems is that they are not universal and only apply to a specific electronic device. Different electronic devices may have different modes of control and would likely need different remote controls, which can be a source of high user friction.

In accordance with the implementations described herein, a technical solution to the above-described technical problem includes a wearable device on a user which translates, via a model, user movements into signals that both identify an electronic device to be controlled. The technical solution to the above-described technical problem also can include a wearable device on a user which translates, via a model, a specific action to take with regard to that electronic device. The wearable device can include an inertial measurement unit (IMU) sensor and a photoplethysmography (PPG) sensor and measure six degrees of freedom (6DOF).

In some implementations, the model used within the wearable device is a convolutional neural network (CNN) that takes x, y, and z-acceleration signals generated by the IMU and PPG and places each acceleration component generated from each sensor in a separate channel. The CNN takes the input from each channel and generates a respective, separate model for each channel. The hidden layers for each model form stacked layers. The output at each of the stacked layers are combined in a fully connected layer to produce CNN output identifying an electronic device and a control for the electronic device.

A technical advantage of the technical solution is that, in contrast to the conventional remote control systems, the system resulting from the technical solution is a universal remote control that can interpret a gesture as identifying an electronic device in the vicinity of a user and then applying a control, based on the gesture, to the electronic device. This decreases user friction and enhances the user experience.

The vicinity of the user is indicated by a region, defined geometrically by either physical boundaries (e.g., bounded by physical walls of a room) or virtual boundaries (e.g., boundaries of a wireless network to which the user and a set of electronic devices are accessing). In some implementations, the vicinity of the user includes an area of specified size and/or diameter that includes the user. Conversely, the user may be in a vicinity of the set of electronic devices; this is equivalent to the set of electronic devices being in the vicinity of the user. In some implementations, the vicinity of the user includes a region defined by an extent of a wireless network (e.g., WiFi) or wireless cell (e.g., LTE, NR). In one example, a set of electronic devices is in a vicinity of the user when the electronic devices are in the same room as the user, or in the same set of rooms as the user. In another example, a set of electronic devices is in a vicinity of the user when the electronic devices are connected to a network to which the computer configured to identify the electronic device and control from a gesture is connected. In the latter case, the user (and/or the computer that identifies the electronic device and control) does not need to be in the same physical location as the set of electronic devices to be in the vicinity of the electronic devices.

FIG. 1A is a diagram that illustrates an example environment 100 in which improved techniques described herein may be implemented. The environment 100 includes a plurality of electronic devices 130(1-5) to be controlled by a user 102. The environment 100 also includes a network 110 for communicating with a computer 120.

In some implementations, the environment 100 is a room in a house or flat. In some implementations, the environment 100 is an office. In some implementations, the environment 100 is at least part of a factory or manufacturing facility. In the latter two cases, silent hand gestures may be preferred due to privacy concerns. In some implementations, the environment 100 is outdoors. In some implementations, the environment 100 is within a vehicle that may or may not be moving.

As shown in FIG. 1A, each of the plurality of electronic devices 130(1-5), e.g., electronic device 130(1), is arranged in the environment 100 in a vicinity of the user 102. It is noted that, while FIG. 1A shows five electronic devices, this is by no means limiting and the improved remote control system may have any number of electronic devices. Being in the vicinity of the user 102 does not necessarily mean that the electronic device 130(1) is located in a line-of-sight to the user 102. For example, the electronic device 130(1) may be located in a different room from the user 102.

In some implementations, at least one of the plurality of electronic devices, e.g., electronic device 130(1), has a camera 132(1) configured to generate an image of a gesture and transmit a signal that represents the image. The camera 132(1) adds context to signals generated by a wearable device 104. For example, the image generated by the camera 132(1) may indicate an electronic device 130(1-5) at which the user's gesture is directed. In order to make use of the camera 132(1), the electronic device 130(1) should be in a line-of-sight arrangement with the user 102.

In some implementations, the user 102 wears a head-mounted wearable device (e.g., a headband, a helmet) that has an embedded camera. In such an implementation, the embedded camera would have a first-person view of the world from the perspective of the user. Moreover, in such an implementation, the embedded camera may have line-of-sight to recognize the user's gestures even when other camera in the environment 100 do not have a line-of-sight.

In some implementations, the environment 100 includes a location server (e.g., electronic device 130(2)) configured to produce a GPS location. Such a GPS location may add additional context to the signals and/or image when transmitted.

As shown in FIG. 1A, the user 102 is wearing a wearable device 104 on their wrist. Further details about the wearable device 104 are shown with regard to FIG. 1B.

Figure 1B:
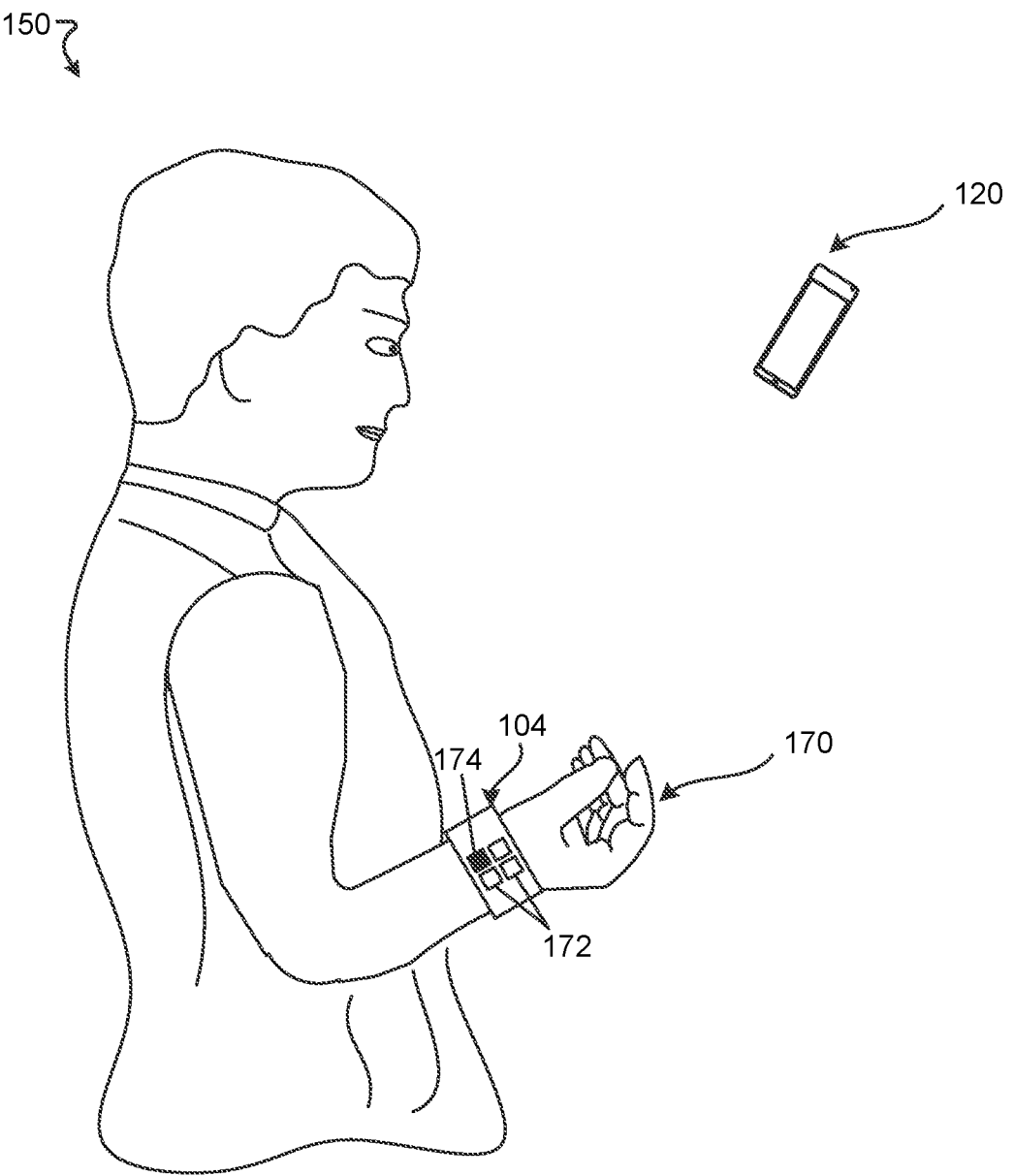
FIG. 1B is a diagram that illustrates an example wearable device used to generate signals for remote control based on user gestures.

FIG. 1B is a diagram that illustrates an environment 150 including an example wearable device 104 used to generate signals for remote control based on user gestures and transmit those signals to the computer 120. As shown in FIG. 1B, the computer 120 is a mobile phone. In some implementations, however, the computer 120 is a desktop, laptop, tablet, server, or the like, as long as the computer 120 is configured to receive data from signals.

As shown in FIG. 1B, the wearable device 104 takes the form of a wristband. The wearable device 104 can take other form factors (e.g., straps). but because the remote control system uses hand gestures, the wearable device is most likely configured to be worn on the wrist.

The wearable device 104 includes sensors 172 and 174 configured to translate a hand gesture 170 formed by the user 102 into signals to be transmitted to the computer 120. In some implementations, the sensors 172 include inertial measurement units (IMUs). An IMU is a device that includes a combination of accelerometers, gyroscopes, and in some cases, magnetometers, in order to measures and reports an acceleration and, in some cases, an orientation.

In some implementations, the sensors 174 include a photoplethysmography (PPG) sensor. A PPG sensor is an optical sensor configured to detect and measure hand micro-movements via exposing small arterial volume changes to optical radiation. Including PPG sensors 174 may make the gesture-based remote control more robust to false positives.

In some implementations, the wearable device 104 includes in sensors 172 and/or 174 a compass. The compass is configured to measure an absolute orientation and provide absolute orientation data in another signal. The absolute orientation may provide additional context as to the orientation of the user's hand as it makes the gesture 170.

During operation, the user 102 forms a gesture with their hand. Upon forming the gesture 170, the user's wrist muscles will move in specific ways, based on the movement of the user's hand in making the gesture 170. The wearable device, upon sensing wrist muscle movement, performs measurements using the IMU sensors 172 and PPG sensors 174. Each of the IMU and PPG sensors 172 and 174 then transmit signal data in the form of a time series to the computer 120. Further details concerning the signals are described with regard to FIG. 4.

In some implementations, the network 110 is a wireless network configured to transmit signal data generated by the wearable device 104 to the computer 120. In some implementations, the wireless network includes a WiFi network that is sourced within the environment 100. In some implementations, the wireless network 110 includes a wireless radio. In some implementations, the wireless radio is one of LTE, LTE-A, 5G (New Radio, or NR), cmWave, and/or mmWave band networks, or any other wireless network.

With continued reference to FIG. 1A, the computer 120 is configured to receive signals generated by the wearable device 104 and apply a CNN model to the received signals to identify an electronic device (e.g., any of electronic devices 130(1-5)). Further details regarding the computer 120 are described in FIG. 2.

FIG. 2 is a diagram that illustrates an example electronic environment 200 in which the above-described technical solution may be implemented. The computer 120 is configured to receive signals generated by the wearable device 104 and apply a CNN model to the received signals to identify an electronic device.

The computer 120 includes a network interface 222, one or more processing units 224, memory 226, and a signal interface 228. The network interface 222 includes, for example, Ethernet adaptors, Token Ring adaptors, and the like, for converting electronic and/or optical signals received from the network to electronic form for use by the computer 120. The set of processing units 224 include one or more processing chips and/or assemblies. The memory 226 includes both volatile memory (e.g., RAM) and non-volatile memory, such as one or more ROMs, disk drives, solid state drives, and the like. The set of processing units 224 and the memory 226 together form controlling circuitry, which is configured and arranged to carry out various methods and functions as described herein. The signal interface 228 is configured to receive signals from the wearable device 104 (FIG. 1A) and represent them as signal data 231.

In some implementations, one or more of the components of the computer 120 can be, or can include processors (e.g., processing units 224) configured to process instructions stored in the memory 226. Examples of such instructions as depicted in FIG. 2 include a signal manager 230, a prediction engine manager 240, and a device and control manager 250. Further, as illustrated in FIG. 2, the memory 226 is configured to store various data, which is described with respect to the respective managers that use such data.

The signal manager 230 is configured to obtain signal data 231. For example, the computer 120, via the signal interface 228, receives signals transmitted by the wearable device 104 in response to a gesture 170 (FIG. 1B) formed by the user 102. The signal manager 230 extracts data carried by the signals and arranges the signal data 231 as shown in FIG. 2.

The signal data 231 represents information about gestures formed by the user 102 from which electronic device identification and control identification may be deduced by a model. The arrangement of the signal data 231 as shown in FIG. 2 is designed for a custom model. As shown in FIG. 2, the signal data includes IMU data 232, PPG data 233, and context data 234.

The IMU data 232 represents signal data as generated by an IMU sensor (e.g., IMU sensor 172 in FIG. 1i). As shown in FIG. 2, IMU data 232 includes components 232(1-M). In some implementations, the components 232(1-M) represent spatial components of the IMU signal (i.e., x, y, z); in this case M=3. In some implementations, the components 232 (1-M) represent acceleration data in (x, y, and z) directions. An example of IMU data component s 232(1-M) are described with regard to FIG. 4.

Figure 4:
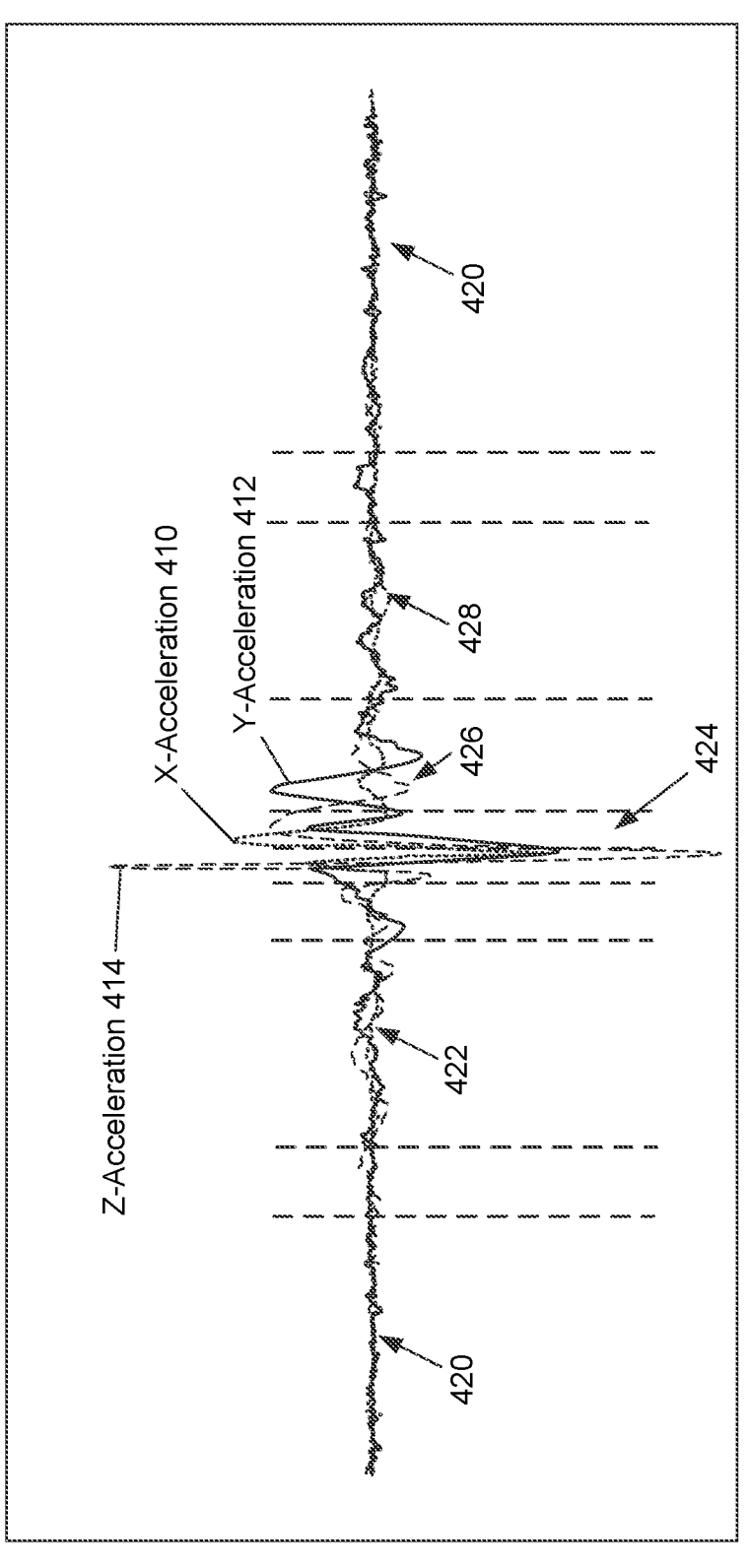
FIG. 4 is a diagram that illustrates an example signal emitted by the user's wearable device in response to the user forming a gesture.

FIG. 4 is a diagram that illustrates an example IMU signal 400 emitted by a user's wearable device in response to the user (e.g., user 102) forming a gesture (e.g., gesture 170) and representing an acceleration of the user's hand when forming the gesture. As shown in FIG. 4, the IMU signal has an x-component 410, a y-component 412, and a z-component 414, each representing respective components of the acceleration. The IN/U signal 400 represents a gesture formed by a click motion with the user's hand.

As shown in FIG. 4, the signal as a function of time may be divided into stages demarcated by dashed lines. For example, stage 420 represents a static (DC) portion where there is no activity. Stage 422 represent a movement of the user's index finger and thumb in the service of starting the click gesture. Stage 424 represents an "impact," in which the index finger and thumb touch to make a "click" motion. Stage 426 represents residual vibrations resulting from the impact. Stage 428 represents a movement of the user's index finger and thumb away from each other to complete the click gesture.

In some implementations, the IMU signals have a higher frame rate than the PPG signals. For example, in one data collection platform, the PPG frame rate was about 100 Hz while the IMU frame rate was about 1000 Hz. A reason for this is that, for example, a click gesture can contain frequency content out to about 200 Hz; by the Nyquist criterion, that would imply a frame rate of at least 400 Hz would be needed.

Returning to FIG. 2, the PPG data 233 represents signal data as generated by a PPG sensor (e.g., PPG sensor 174 in FIG. 1). As shown in FIG. 2, PPG data 233 includes components 233(1-M). In some implementations, the components 233(1-M) represent spatial components of the PPG signal (i.e., x, y, z); in this case M=3. In some implementations, the components 233(1-M) represent acceleration data in (x, y, and z) directions.

In some implementations, the context data 234 represents additional signal information received at the signal interface 228. The context data 234, in concert with the IMU data 232 and PPG data 233, may provide more robustness of the control result. As shown in FIG. 2, the context data 234 includes compass data 235, camera data 236, and GPS data 237. In some implementations, the context data 234 includes one or two of the data 235, camera data 236, and GPS data 237.

The compass data 235 represents an absolute orientation of the hand of the user 102 which forms the gesture 170. In some implementations, the compass that generates the compass data 235 is included in the wearable device 104.

The camera data 236 represents an image of the gesture 170 formed by the user 102. As described above, the camera data 236 may be formed by cameras on electronic devices that are arranged to have a line-of-sight with respect to the user 102. The camera data 236 may be useful in, for example, determining orientations of "pointing" gestures.

The GPS data 237 represents a location of the user. In some implementations, the GPS data is generated by a GOS device built into the wearable device 104.

The prediction engine manager 240 is configured to arrange the signal data 231 into channels within prediction engine data 241 and generate the output device and control identifications. The prediction engine manager 240 is also configured to generate separate models for each of the channels; in this respect, the prediction engine manager is configured to train each of the models based on gesture data from a population of users. The prediction engine manager 240 is configured to combine the output from each of these models to produce combined data from which the identifications of the electronic device and control may be derived.

The prediction engine data 241 represents the inputs, model parameter values, and outputs used and generated by the prediction engine manager 240. The models trained and evaluated by the prediction engine manager 240 are convolutional neural networks (CNNs). Before describing the elements of the models, the overall model is described with regard to FIG. 3.

Figure 3:
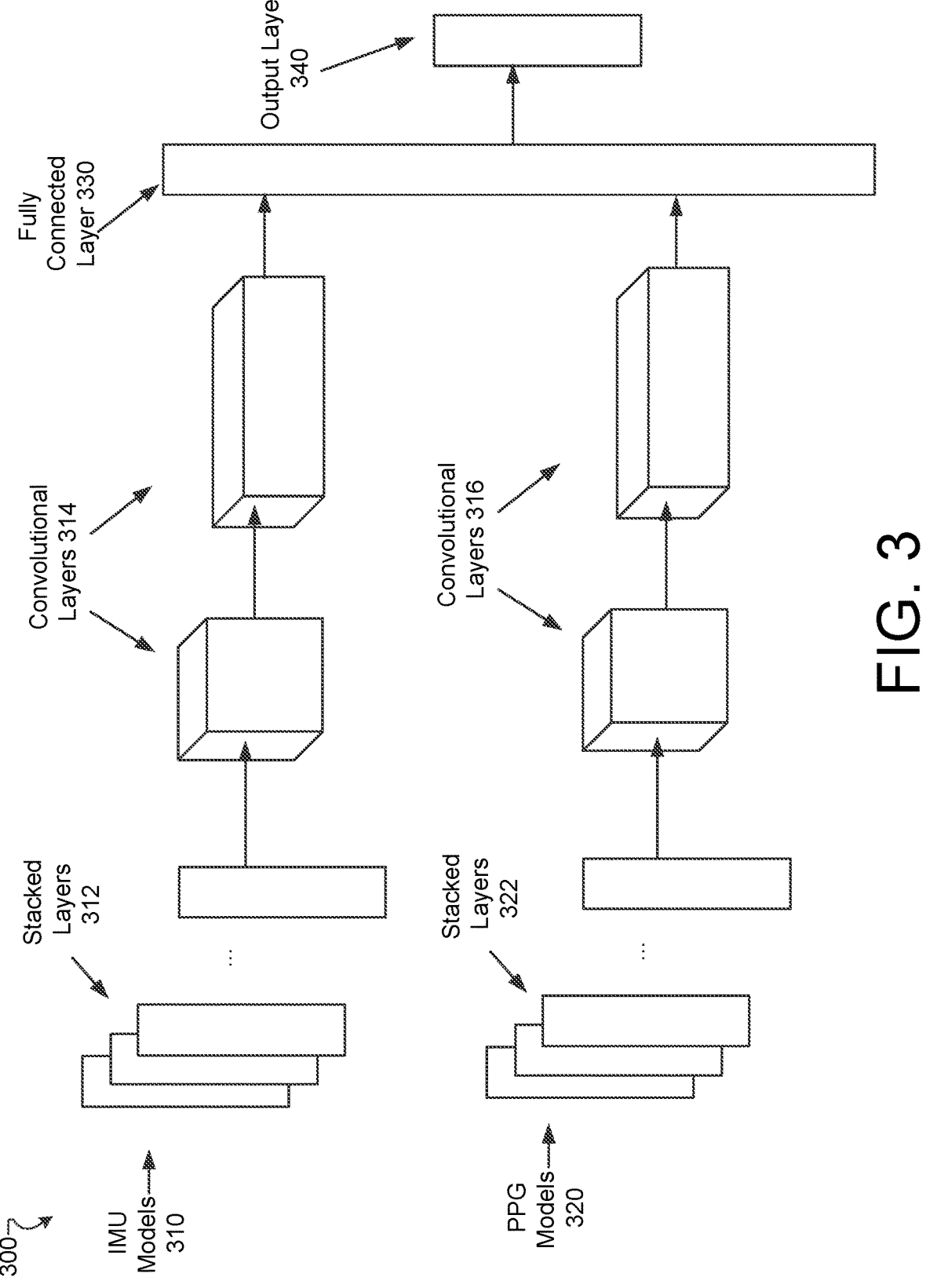
FIG. 3 is a diagram that illustrates an example convolu-tional neural network (CNN) with stacked layers for differ-ent channels.

FIG. 3 is a diagram that illustrates an example CNN 300 with stacked layers as model input for different channels. As shown in FIG. 3, the CNN model 300 places each signal component from each signal source in stacked layers. For example, the IMU models 310 input each spatial component of the IMU signal into stacked layers 312 and the PPG models 320 input each component of the PPG signal into stacked layers 322. That is, data from the channel containing the x-acceleration signal 410 (FIG. 4) is put into an input layer of a dedicated CNN model for the IMU x-acceleration. The data from the channels containing the IMU y- and z-acceleration signals 412 and 414, respectively, is similarly put into input layers of dedicated CNN models for the IMU y- and z-acceleration. PPG signal components are similarly put into input layers of their respective dedicated CNN models.

As shown in FIG. 3, the input data in the IMU stacked layers 312 are fed into intermediate, hidden convolutional layers 314. Similarly, the input data in the PPG stacked layers 322 are fed into intermediate, hidden convolutional layers 316. Again, each signal component from each device is processed in its own, respective model. Using separate models in this fashion enhances the accuracy of the predictions.

Also as shown in FIG. 3, the values of the final convolutional layers 314 and 316 are then input into a fully connected layer 330. In the fully connected layer 330, the values of each signal component from each source are combined to produce a single set of values to be input into an output layer 340. From these single values, the overall model selects an electronic device and a control for that electronic device.

Returning to FIG. 2, the prediction engine data 241 includes stacked layer data 242 and model data 243.

The stacked layer data 242 represents the signal components from each channel corresponding to a respective signal source (e.g., IMU, PPG, context). Each channel of the stacked layer data 242 is input into its own respective model represented by model data 243. As shown in FIG. 2, the stacked layer data 242 includes channel data 242(1-P), where P is the number of signal components and sources.

Each channel data 242(1-P), e.g., channel data 242(1), represents an amplitude and/or phase of a signal component from a sensor. That is, channel data 242(1) may represent an IMU x-acceleration, channel data 242(2) represents an IMU y-acceleration, and so on. Some channel data, e.g., 242(4) may represent a PPG signal component. Nevertheless, in some implementations, each channel data 242(1-P) includes streaming values that form a time series.

The model data 243 represents data defining the channel models 243(1-P) corresponding to each of the channel data 242(1-P). Each model, e.g., 243(1) includes parameter values corresponding to each convolutional layer 243(1)(1-R1) in each model, where R1 is the number of convolutional layers in the model corresponding to channel data 242(1). In some implementations, the number of parameters is less than 10,000. Moreover, each model, e.g., 243(1) may or may not include pooling layers, skip layers, and nonlinear activation functions. In some implementations, the models are trained in a supervisor framework using a loss function based on a difference between predicted results and actual results.

As shown in FIG. 2, the prediction engine data 241 also includes fully connected layer data 244 and output layer data 245. The fully connected layer data 244 is configured to take in the outputs of each channel model represented by channel model data 243(1-P), i.e., the values in convolution layers 243(1)(R1)-243(P)(RP), and combine them to produce values for the output layer 245. In some implementations, the combining of the values in convolution layers 243(1)(R1)-243(P)(RP) is a concatenation of those values, i.e., the output of each convolutional layer are stacked end-to-end to form the fully connected layer. In some implementations, the results are averaged. In some implementations, the averaging is weighted based on a criterion.

The device and control manager 250 is configured to perform a control identified by device control data 252 on an electronic device identified by device identification data 251. The device identification data 251 and the device control data 252 are based on the output layer data 245, i.e., the output of the overall CNN model; in some implementations, the identification data 251 and 252 are in the output layer data 245.

In some implementations, another output of the CNN model used by the device and control manager 250 is resolution data 253. Resolution data 253 includes an indication of whether a pair of electronic devices are too close together. In the case that the resolution data 253 indicates a pair of electronic devices too close together to arbitrate which electronic device is intended by the user, the resolution data 253 also represents rules for deciding which of the electronic devices to select.

The components (e.g., modules, processing units 224) of computer 120 can be configured to operate based on one or more platforms (e.g., one or more similar or different platforms) that can include one or more types of hardware, software, firmware, operating systems, runtime libraries, and/or so forth. In some implementations, the components of the computer 120 can be configured to operate within a cluster of devices (e.g., a server farm). In such an implementation, the functionality and processing of the components of the computer 120 can be distributed to several devices of the cluster of devices.

The components of the computer 120 can be, or can include, any type of hardware and/or software configured to process attributes. In some implementations, one or more portions of the components shown in the components of the computer 120 in FIG. 2 can be, or can include, a hardware-based module (e.g., a digital signal processor (DSP), a field programmable gate array (FPGA), a memory), a firmware module, and/or a software-based module (e.g., a module of computer code, a set of computer-readable instructions that can be executed at a computer). For example, in some implementations, one or more portions of the components of the computer 120 can be, or can include, a software module configured for execution by at least one processor (not shown). In some implementations, the functionality of the components can be included in different modules and/or different components than those shown in FIG. 2, including combining functionality illustrated as two components into a single component.

Although not shown, in some implementations, the components of the computer 120 (or portions thereof) can be configured to operate within, for example, a data center (e.g., a cloud computing environment), a computer system, one or more server/host devices, and/or so forth. In some implementations, the components of the computer 120 (or portions thereof) can be configured to operate within a network. Thus, the components of the computer 120 (or portions thereof) can be configured to function within various types of network environments that can include one or more devices and/or one or more server devices. For example, the network can be, or can include, a local area network (LAN), a wide area network (WAN), and/or so forth. The network can be, or can include, a wireless network and/or wireless network implemented using, for example, gateway devices, bridges, switches, and/or so forth. The network can include one or more segments and/or can have portions based on various protocols such as Internet Protocol (IP) and/or a proprietary protocol. The network can include at least a portion of the Internet.

In some implementations, one or more of the components of the search system can be, or can include, processors configured to process instructions stored in a memory. For example, signal manager 230 (and/or a portion thereof), a prediction engine manager 240 (and/or a portion thereof), and device and control manager 250 (and/or a portion thereof)

In some implementations, the memory 226 can be any type of memory such as a random-access memory, a disk drive memory, flash memory, and/or so forth. In some implementations, the memory 226 can be implemented as more than one memory component (e.g., more than one RAM component or disk drive memory) associated with the components of the computer 120. In some implementations, the memory 226 can be a database memory. In some implementations, the memory 226 can be, or can include, a non-local memory. For example, the memory 226 can be, or can include, a memory shared by multiple devices (not shown). In some implementations, the memory 226 can be associated with a server device (not shown) within a network and configured to serve the components of the computer 120. As illustrated in FIG. 2, the memory 226 is configured to store various data, including signal data 231 including IMU data 232, PPG data 233 and context data 234, prediction engine data 241 including stacked layer data 242, model data 243, FC layer data 244, and output layer data 245.

FIG. 5 is a flow chart depicting an example method 500 of identifying and controlling an electronic device using hand gestures. The method 500 may be performed by software constructs described in connection with FIG. 2, which reside in memory 226 of the computer 120 and are run by the set of processing units 224.

At 502, the signal manager 230 receives, from a wearable device (e.g., wearable device 104) worn by a user (e.g., user 102), the user located in a vicinity of a plurality of electronic devices (e.g., electronic devices 130(1-5)), signal data (e.g., signal data 231) representing user movements of the user as detected by the wearable device.

At 504, the prediction engine manager 240 inputs the signal data into a model (e.g., prediction engine data 241) to identify an electronic device of the plurality of the electronic devices and a control to be applied to the identified electronic device.

At 506, the device and control manager 250 applies the control to the identified electronic device.

Figure 6:
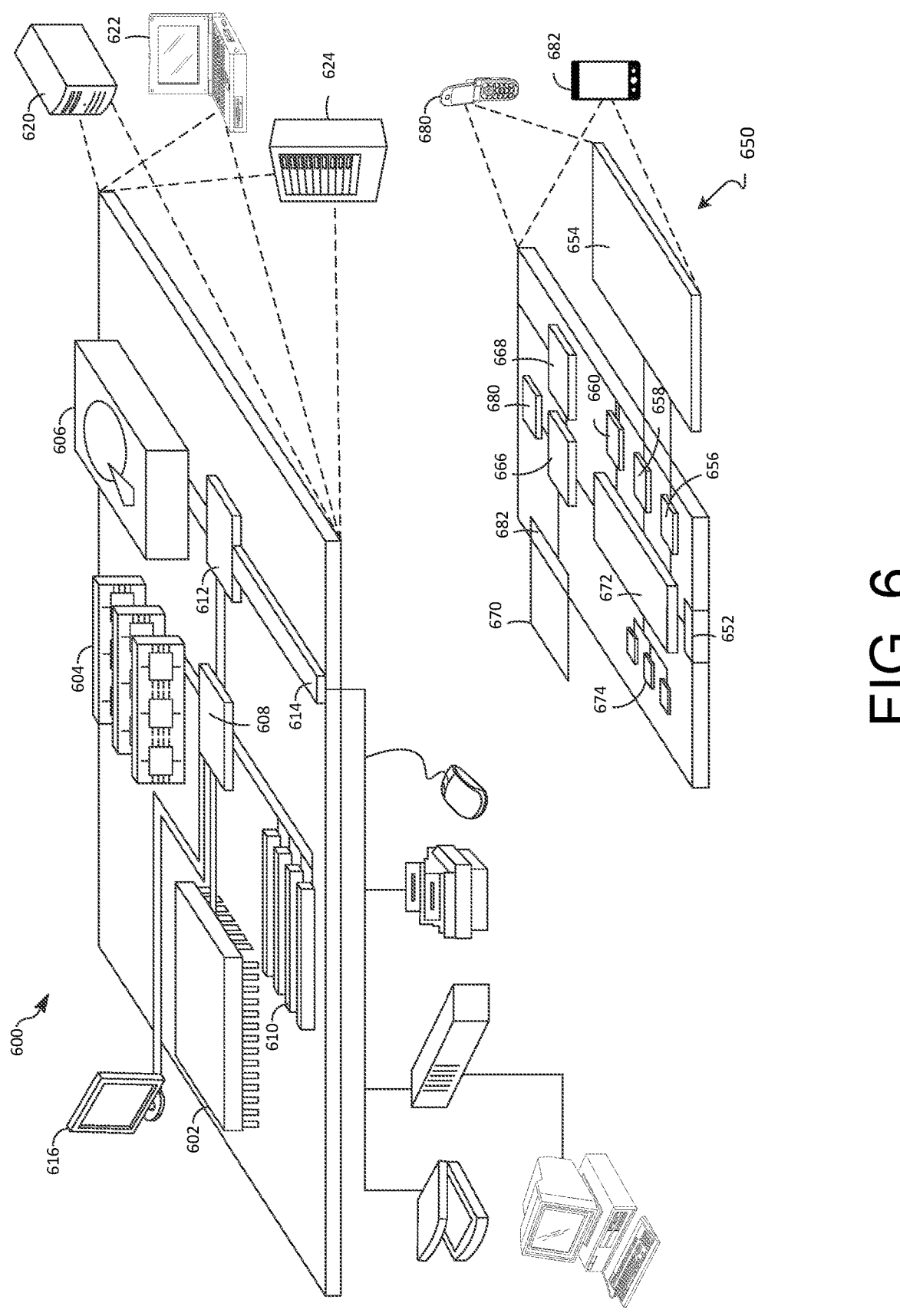
FIG. 6 is a diagram that illustrates an example of a computer device and a mobile computer device that can be used to implement the described techniques.

FIG. 6 illustrates an example of a generic computer device 600 and a generic mobile computer device 650, which may be used with the techniques described here. Computer device 600 is one example configuration of computer 120 of FIG. 2.

As shown in FIG. 6, computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smart phones, and other similar computing devices. The components shown here, their connections and relationships, and their functions, are meant to be examples only, and are not meant to limit implementations of the inventions described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a volatile memory unit or units. In another implementation, the memory 604 is a non-volatile memory unit or units. The memory 604 may also be another form of computer-readable medium, such as a magnetic or optical disk.

The storage device 606 is capable of providing mass storage for the computing device 600. In one implementation, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 604, the storage device 606, or memory on processor 602.

The high speed controller 608 manages bandwidth-intensive operations for the computing device 600, while the low speed controller 612 manages lower bandwidth-intensive operations. Such allocation of functions are examples only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 506 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can execute instructions within the computing device 650, including instructions stored in the memory 664. The processor may be implemented as a chipset of chips that include separate and multiple analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD (Thin-Film-Transistor Liquid Crystal Display) or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 660 may be provided in communication with processor 652, so as to enable near area communication of device 650 with other devices. External interface 660 may provide, for example, for wired communication in some implementations, or for wireless communication in other implementations, and multiple interfaces may also be used.

The memory 664 stores information within the computing device 650. The memory 664 can be implemented as one or more of a computer-readable medium or media, a volatile memory unit or units, or a non-volatile memory unit or units. Expansion memory 674 may also be provided and connected to device 650 through expansion interface 672, which may include, for example, a SIMM (Single In Line Memory Module) card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provided as a security module for device 650, and may be programmed with instructions that permit secure use of device 650. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory, expansion memory 674, or memory on processor 652, that may be received, for example, over transceiver 668 or external interface 660.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS (Global Positioning System) receiver module 670 may provide additional navigation- and location-related wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smart phone 682, personal digital assistant, or other similar mobile device.

Figure 7:
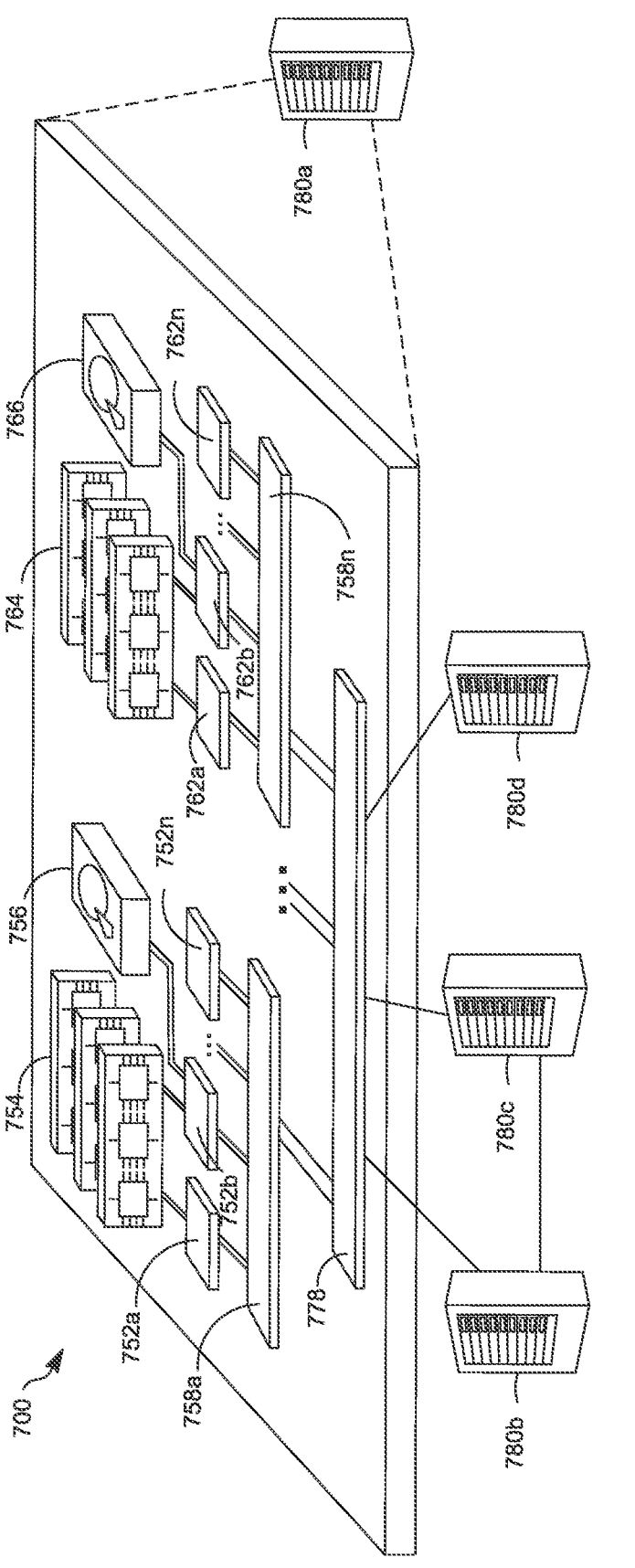
FIG. 7 is a diagram that illustrates an example of a distributed computer device that can be used to implement the described techniques.

FIG. 7 shows an example of a generic computer device 700, which may be computer 120 of FIG. 2, which may be used with the techniques described here. Computing device 700 is intended to represent various example forms of large-scale data processing devices, such as servers, blade servers, datacenters, mainframes, and other large-scale computing devices. Computing device 700 may be a distributed system having multiple processors, possibly including network attached storage nodes, that are interconnected by one or more communication networks. The components shown here, their connections and relationships, and their functions, are meant to be examples only, and are not meant to limit implementations of the inventions described and/or claimed in this document.

Distributed computing system 70 may include any number of computing devices 780. Computing devices 780 may include a server or rack servers, mainframes, etc. communicating over a local or wide-area network, dedicated optical links, modems, bridges, routers, switches, wired or wireless networks, etc.

In some implementations, each computing device may include multiple racks. For example, computing device 780a includes multiple racks 758a-758n. Each rack may include one or more processors, such as processors 752a-752n and 762a-762n. The processors may include data processors, network attached storage devices, and other computer controlled devices. In some implementations, one processor may operate as a master processor and control the scheduling and data distribution tasks. Processors may be interconnected through one or more rack switches 762a-762n, and one or more racks may be connected through switch 778. Switch 778 may handle communications between multiple connected computing devices 700.

Each rack may include memory, such as memory 754 and memory 764, and storage, such as 756 and 766. Storage 756 and 766 may provide mass storage and may include volatile or non-volatile storage, such as network-attached disks, floppy disks, hard disks, optical disks, tapes, flash memory or other similar solid state memory devices, or an array of devices, including devices in a storage area network or other configurations. Storage 756 or 766 may be shared between multiple processors, multiple racks, or multiple computing devices and may include a computer-readable medium storing instructions executable by one or more of the processors. Memory 754 and 764 may include, e.g., volatile memory unit or units, a non-volatile memory unit or units, and/or other forms of computer-readable media, such as a magnetic or optical disks, flash memory, cache, Random Access Memory (RAM), Read Only Memory (ROM), and combinations thereof. Memory, such as memory 754 may also be shared between processors 752a-752n. Data structures, such as an index, may be stored, for example, across storage 756 and memory 754. Computing device 700 may include other components not shown, such as controllers, buses, input/output devices, communications modules, etc.

An entire system, such as environment 100 of FIG. 1A, may be made up of multiple computing devices 700 communicating with each other. For example, device 780a may communicate with devices 780b, 780c, and 780d, and these may collectively be known as environment 100. As another example, computer 120 of FIG. 2 may include one or more computing devices 700. Some of the computing devices may be located geographically close to each other, and others may be located geographically distant. The layout of system 700 is an example only and the system may take on other layouts or configurations.

In some implementations, the model is a convolutional neural network (CNN) configured to take the signal data as input and produce a device identifier for the identified electronic device of the plurality of electronic devices and a control identifier for the control.

In some implementations, the wearable device worn by the user includes a set of electronic sensors, each of the electronic sensors being configured to produce the signal data in response to detecting the user movements.

In some implementations, the set of sensors includes an inertial measurement unit (IMU) sensor. In some implementations, the set of sensors includes a photoplethysmography (PPG) sensor.

In some implementations, the CNN includes a plurality of stacked layers, each of the plurality of stacked channels corresponding to a respective electronic sensor of the set of electronic sensors.

In some implementations, each of the plurality of stacked layers of the CNN represents a representing model component. In such an implementation, the method further includes training a first model component represented by a first stacked layer of the plurality of stacked layers; and training a second model component represented by a second stacked layer of the plurality of stacked layers independently of the training of the first model component. In such implementations, the method can further include combining model components represented by the plurality of stacked layers at a fully connected layer of the CNN.

In some implementations, the CNN includes a plurality of stacked layers, each of the plurality of stacked layers corresponding to a respective degree of freedom of the user movements.

In some implementations, the signal data further represents a set of context signals, the context signals having been generated from other sensors apart from the wearable device. In some implementations, the context signals originate at a compass and indicate a direction at which the user movements are directed. In some implementations, the context signals include an image of a gesture formed by the user from a camera embedded in an electronic device. In some implementations, the context signals originate at a global positioning system (GPS) and indicate a location of the user.

In some implementations, the model is configured to output a device identifier identifying the electronic device and a control identifier identifying the control. In some implementations, the model is further configured to output a spacing indicator indicating whether a first electronic device and a second electronic device of the plurality of electronic devices are spaced sufficiently apart for robust identification output by the model.

In some implementations, the model is configured to determine whether the user movements form a recognized gesture.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made without departing from the spirit and scope of the specification.

It will also be understood that when an element is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element, there are no intervening elements present. Although the terms directly on, directly connected to, or directly coupled to may not be used throughout the detailed description, elements that are shown as being directly on, directly connected or directly coupled can be referred to as such. The claims of the application may be amended to recite example relationships described in the specification or shown in the figures.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A method comprising:
    receiving signal data from a wearable device, the signal data representing a motion as detected by an electronic sensor, the signal data having a first component input into a first model to produce a first output, the signal data having a second component input into a second model to produce a second output, the first model and the second model being included in an overall model;

combining the first output and the second output at a connected layer of the overall model to identify an electronic device and identify an instruction to be sent to the electronic device; and sending the instruction to the electronic device.

2. The method as in claim 1, wherein the overall model includes a convolutional neural network (CNN).

3. The method as in claim 2, wherein the CNN includes a first stacked layer corresponding to the first component and a second stacked layer corresponding to the second component.

4. The method as in claim 3, wherein the method further comprises:

training the first model to produce a trained first model; and training the second model independently of the trained first model.

5. The method as in claim 2, wherein the CNN includes a plurality of stacked layers corresponding to a degree of freedom of the motion.

6. The method as in claim 2, wherein additional signal data is input into the CNN, the additional signal data representing a context signal, the context signal having been generated from a sensor apart from the wearable device.

7. The method as in claim 6, wherein the context signal originates at a compass and indicates a direction at which the motion is directed.

8. The method as in claim 6, wherein the context signal includes an image of a gesture from a camera.

9. The method as in claim 6, wherein the context signal originates at a global positioning system (GPS) and indicates a location.

10. The method as in claim 2, wherein the CNN is configured to output a spacing indicator indicating whether a first electronic device and a second electronic device are spaced sufficiently apart for robust identification.

11. The method as in claim 2, wherein the CNN is configured to determine whether the motion forms a recognized gesture.

12. The method as in claim 1, wherein the electronic sensor is an inertial measurement unit (IMU) sensor.

13. The method as in claim 1, wherein the electronic sensor is a photoplethysmography (PPG) sensor.

14. The method as in claim 1, wherein the wearable device and the electronic device are located within a room, bounded by physical walls.

15. A non-transitory storage medium including code that, when executed by processing circuitry, causes the processing circuitry to perform a method, the method comprising:

receiving signal data from a wearable device, the signal data representing a motion as detected by an electronic sensor, the signal data having a first component input into a first model to produce a first output, the signal data having a second component input into a second model to produce a second output, the first model and the second model being included in an overall model configured to identify an electronic device;

combining the first output and the second output at a connected layer of the overall model to identify an electronic device and identify an instruction to be sent to the electronic device; and sending the-instruction to the electronic device.

16. The non-transitory storage medium as in claim 15, wherein the overall model includes a convolutional neural network (CNN).

17. The non-transitory storage medium as in claim 16, wherein the CNN includes a first stacked layer corresponding to the first component and a second stacked layer corresponding to the second component, and wherein the method further comprises:

training the first model to produce a trained first model; and training the second model independently of the trained first model.

18. An apparatus, the apparatus comprising:

memory; and controlling circuitry coupled to the memory, the controlling circuitry being configured to:

receive signal data from a wearable device, the signal data representing a motion as detected by an electronic sensor, the signal data having a first component input into a first model to produce a first output, the signal data having a second component input into a second model to produce a second output, the first model and the second model being included in an overall model;

combine the first output and the second output at a connected layer of the overall model to identify an electronic device and identify an instruction to be sent to the electronic device; and send the instruction to the electronic device.

19. The apparatus as in claim 18, wherein the overall model includes a convolutional neural network (CNN).

* * * * *